US009586936B2

(12) United States Patent
Sim et al.

(10) Patent No.: US 9,586,936 B2
(45) Date of Patent: Mar. 7, 2017

(54) HETEROARYLAMINE DERIVATIVES AS PROTEIN KINASE INHIBITORS

(71) Applicant: KOREA INSTITUTE OF SCIENCE AND TECHNOLOGY, Seoul (KR)

(72) Inventors: Tae Bo Sim, Seoul (KR); Ho Jong Yoon, Seoul (KR); Ji Hye Yoon, Seoul (KR); Woo Young Hur, Seoul (KR); Eun Joo Roh, Seoul (KR); Yeon Ui Kwak, Seoul (KR)

(73) Assignee: KOREA INSTITITUE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/947,204

(22) Filed: Nov. 20, 2015

(65) Prior Publication Data

US 2016/0145240 A1    May 26, 2016

(30) Foreign Application Priority Data

Nov. 26, 2014 (KR) ........................ 10-2014-0166484

(51) Int. Cl.
| | |
|---|---|
| *A61K 31/506* | (2006.01) |
| *C07D 403/04* | (2006.01) |
| *C07D 401/14* | (2006.01) |
| *C07D 471/04* | (2006.01) |
| *C07D 487/04* | (2006.01) |

(52) U.S. Cl.
CPC ......... *C07D 403/04* (2013.01); *C07D 401/14* (2013.01); *C07D 471/04* (2013.01); *C07D 487/04* (2013.01)

(58) Field of Classification Search
CPC .. C07D 403/04; C07D 401/14; C07D 471/04; C07D 487/04
See application file for complete search history.

(56) References Cited

U.S. PATENT DOCUMENTS

2012/0165334 A1* 6/2012 Boezio ................. C07D 401/14
514/245

FOREIGN PATENT DOCUMENTS

KR  10-2008-0015475 A    2/2008
WO  WO 2007005673 A1 *  1/2007 ........... C07D 401/14

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
W. Xie et al., International Journal of Quantum Chemistry, 598-609 (2014).*
E. Peterson et al., 21 Bioorganic & Medicinal Chemistry Letters, 2064-2070 (2011).*
F. Wu et al., 4 MedChemComm 1482-1496 (2013).*
G. Zhang et al., 19 Bioorganic & Medicinal Chemistry Letters, 6691-6695 (2009).*
G. Zhange et al., Bioorganic & Medicinal Chemistry Letters, 5618-5621 (2008).*
Guagnano et al., Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), a Potent and Selective Inhibitor of the Fibroblast Growth Factor Receptor Family of Receptor Tyrosine Kinase, Journal of Medicinal Chemistry, Sep. 21, 2011, 7066-7083, 54, ACS Publications.
G.Zhang et al. Discovery of pyrimidine benzimidazoles as Src-family selective Lck inhibitors.Part II, Bioorganic & Medicinal Chemistry Letters 19 ,Oct. 12, 2009, pp. 6691-6695, Elsevier.
G.Zhang et al., Discovery of pyrimidine benzimidazoles as Lck inhibitors: Part I, Bioorganic & Medicinal Chemistry Letters 18, Aug. 31, 2008, pp. 5618-5621, Elsevier.
Xie et al.,3D-QSAR Studies and Molecular Design on a Novel Series of Pyrimidine Benzimidazoles as Lck Inhibitors, International Journal of Quantum Chemistry, 2014, pp. 598-609, vol. 114.
E. A. Peterson et al., Discovery of triazine-benzimidazoles as selective inhibitors of mTOR, Bioorganic & Medicinal Chemistry Letters 21,Feb. 2011, pp. 2064-2070, Elsevier.
Wu et al., Exploring the selectivity of PI3Ka and mTOR inhibitors by 3D-QSAR, molecular dynamics simulations and MM/GBSA binding free energy decomposition, Sep. 9, 2013, | Med. Chem. Commun., 2013, pp. 1482-1496, vol. 4.
Communications of international Search report, PCT/KR2015/012610 issued on Jul. 27, 2016, which corresponds to this application.

* cited by examiner

*Primary Examiner* — Alexander R Pagano
(74) *Attorney, Agent, or Firm* — Goldilocks Zone IP Law

(57) ABSTRACT

A heteroarylamine compound includes protein kinase inhibition activity, a pharmaceutically acceptable salt thereof and a pharmaceutical composition for preventing and treating a disease caused by abnormal cell growth, which contains the compound as an active ingredient.

11 Claims, 1 Drawing Sheet

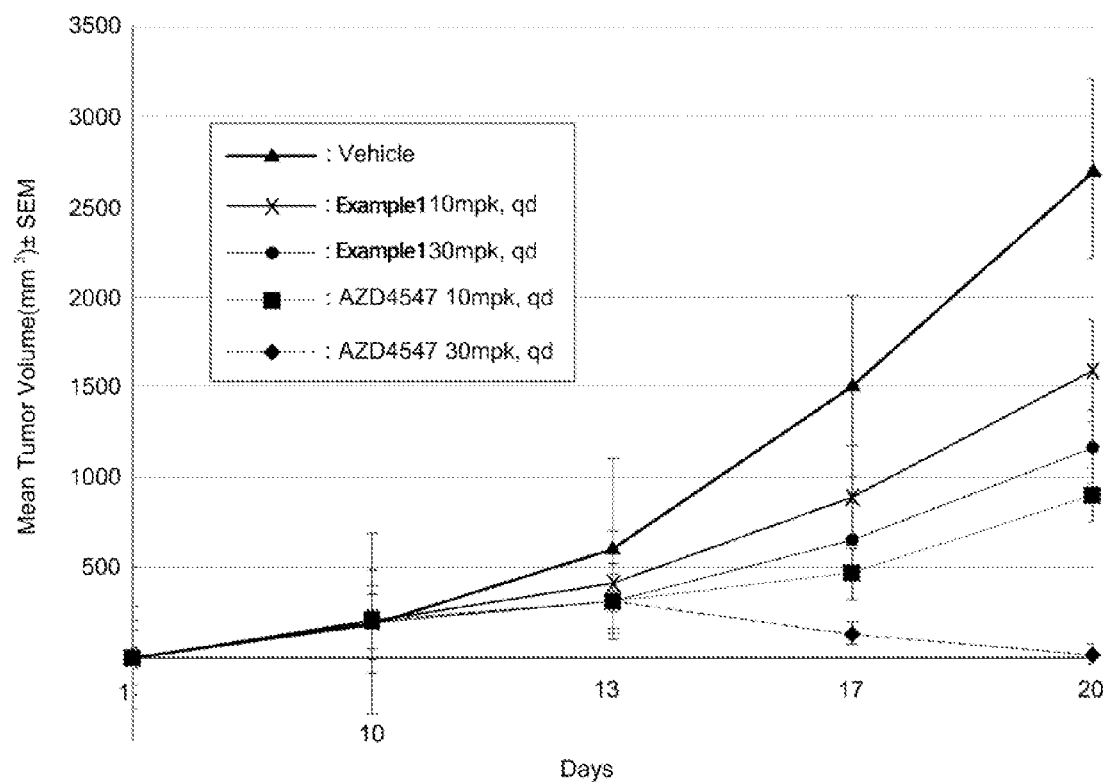

HETEROARYLAMINE DERIVATIVES AS PROTEIN KINASE INHIBITORS

CROSS-REFERENCE TO RELATED APPLICATIONS

This application claims, under 35 U.S.C. §119, the priority of Korean Patent Application No. 10-2014-0166484, filed on Nov. 26, 2014, in the Korean Intellectual Property Office, the disclosure of which is incorporated herein by reference in its entirety.

BACKGROUND

(a) Technical Field

The present invention relates to a novel heteroarylamine derivative having an effect of inhibiting a protein kinase and a pharmaceutical composition for preventing and treating cancer induced by abnormal cell growth, which contains the novel compound as an active ingredient.

(b) Background Art

Fibroblast growth factors (FGFs) and their receptors regulate various biological development processes including tissue regeneration, hematopoiesis, angiogenesis, embryonic development, etc. The FGF receptors (FGFRs) are divided into 4 subtypes which share extracellular ligand-binding domains, hydrophobic transmembrane domains and intracellular kinase domains. FGFR dimerization occurs when an FGF ligand is bound to the FGFR. Subsequently, the activation of downstream signaling pathways is induced by autophosphorylation and the above-described various biological development processes are regulated.

Recently, FGFs and FGFRs are drawing attentions as oncogenes acting as major proliferation factors in cancer cells resistant to various anticancer drugs. Abnormal FGFR-mediated signal transduction induces breast cancer, multiple myeloma, bladder cancer, endometrial cancer, stomach cancer, prostate cancer, etc. The carcinogenesis of various cancers associated with FGFR is caused by the overexpression of the receptor due to proliferation of the gene and abnormal transcriptional regulation. As a result, the cancer cells acquire high sensitivity to the FGF ligand or proliferate via a mechanism of autoactivation through dimerization independently of the ligand.

The inhibition of the FGF/FGFR signal transduction system for anticancer therapy is very important in the development of kinase-based anticancer drugs. At present, a number of compounds (e.g., BIBF-1120, SU6668, NVP-BGJ398, AZD4547) are under clinical trials. Because these compounds are FGFR inhibitors with poor selectivity, it is difficult to pharmacologically identify the anticancer mechanism through inhibition of FGFR. Accordingly, a novel FGFR inhibitor with good selectivity and high activity needs to be developed.

J. Med. Chem. 2011, 54, 7066-7083 discloses that the compound 3-(2,6-dichloro-3,5-dimethoxyphenyl)-1-{6-[4-(4-ethyl-piperazin-1-yl)phenylamino]pyrimidin-4-yl}-1-methylurea (NVP-BGJ398) has selective inhibition activity against FGFR3 and exhibits effective anticancer activity for the RT112 bladder cancer cell line.

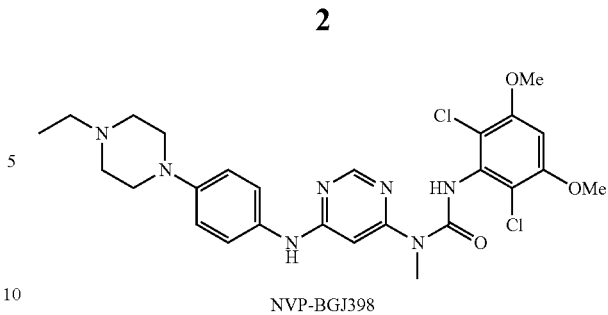

NVP-BGJ398

Until now, several compounds having benz[d]imidazol-2-amine as a backbone have been synthesized. But, the heteroarylamine compound of the present invention has never been reported. In addition, the inhibition activity of the heteroarylamine compound of the present invention against a protein kinase and its use for treatment and prevention of tumors have not been predicted yet.

REFERENCES OF THE RELATED ART

Non-Patent Document (Non-patent document 1) J. Med. Chem. 2011, 54, 7066-7083.

SUMMARY

The present invention is directed to providing a novel compound having specific substituents for a heteroarylamine backbone or a pharmaceutically acceptable salt thereof.

The present invention is also directed to providing a pharmaceutical composition for preventing and treating a disease caused by abnormal cell growth, which contains the novel compound or a pharmaceutically acceptable salt thereof as an active ingredient.

The present invention is also directed to providing a method for preparing the novel compound.

The present invention is also directed to providing a novel intermediate compound synthesized during the process of the above-described preparation method.

In an aspect, the present invention provides a compound selected from a heteroarylamine compound represented by Chemical Formula 1, a pharmaceutically acceptable salt thereof, a hydrate thereof and a solvate thereof.

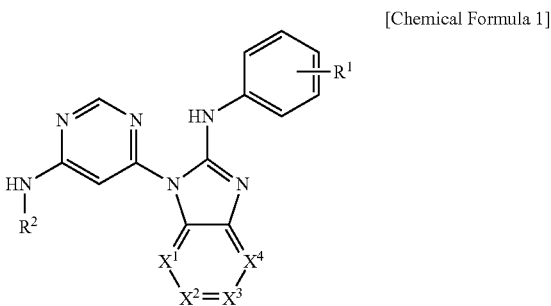

[Chemical Formula 1]

In Chemical Formula 1,
each of $X^1$, $X^2$, $X^3$ and $X^4$ is N or CH,
$R^1$ is one to four substituent(s) selected from a halogen atom, $C_1$-$C_8$ alkyl, $C_1$-$C_8$ alkoxy and

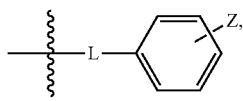

$R^2$ is a hydrogen atom, $C_1$-$C_8$ alkyl, —$(CH_2)_m$—$NR^3R^4$ or -A-$(CH_2)_n$-$(Q)_p$-$R^5$, A is $C_6$-$C_{15}$ aryl, 5- or 6-membered heteroaryl containing one to three nitrogen atom(s) or 5- or 6-membered heterocycloalkyl containing one to three heteroatom(s) selected from a nitrogen atom and an oxygen atom, wherein each of the aryl, heteroaryl or heterocycloalkyl may be substituted or unsubstituted with one to three substituent(s) selected from $C_1$-$C_8$ alkyl, $C_1$-$C_8$ alkoxy, $C_1$-$C_8$ haloalkyl and $C_1$-$C_8$ alkoxycarbonyl, L is —NHC(O)— or —C(O)NH—, Z is one to four substituent(s) selected from $C_1$-$C_8$ alkyl, $C_1$-$C_8$ haloalkyl, 5- or 6-membered heteroaryl containing one to three nitrogen atom(s) and 5- or 6-membered heterocycloalkyl containing one to three heteroatom(s) selected from a nitrogen atom and an oxygen atom, wherein the heteroaryl or heterocycloalkyl may be substituted or unsubstituted with $C_1$-$C_8$ alkyl, Q is 5- or 6-membered heterocycloalkyl or biheterocycloalkyl containing one to three heteroatom(s) selected from a nitrogen atom and an oxygen atom, each of $R^3$ and $R^4$ is a hydrogen atom or $C_1$-$C_8$ alkyl, $R^5$ is a hydrogen atom, $C(O)OR^7$ (wherein $R^7$ is a hydrogen atom or $C_1$-$C_8$ alkyl) or $C_1$-$C_8$ alkyl, m is an integer from 1 to 6, n is an integer from 0 to 6, and p, which indicates the presence or absence of Q, is 0 or 1.

Since the compound of the present invention exhibits a superior effect of inhibiting the activity of a protein kinase selected from ABL2, ACK1, ALK, BLK, BMX, c-Kit, c-Src, DDR1, DDR2, DYRK1, DYRK1B, DYRK2, EGFR, HER2, FGFR1, FGFR2, FGFR3, FGFR4, FGF, FLT3, FLT4, FMS, Fyn, Hck, MAP4K5, LCK, LIMK1, LYN, LYN B, MEKK2, MEKK3, ROS, SIK1, SIK2, SIK3, TAOK1, TAOK2, TIE2, TNK1, TRKA and YES, it can be used as an active ingredient of a pharmaceutical composition for preventing and treating a disease caused by abnormal cell growth.

Accordingly, the compound according to the present invention can be used for preventing and treating diseases caused by abnormal cell growth, for example, various tumor diseases selected from endometrial cancer, bladder cancer, stomach cancer, lung cancer, liver cancer, colon cancer, small intestine cancer, pancreatic cancer, brain cancer, bone cancer, melanoma, breast cancer, sclerosing adenosis, head and neck cancer, esophageal cancer, thyroid cancer, parathyroid cancer, kidney cancer, sarcoma, prostate cancer, urethral cancer, blood cancer such as leukemia, multiple myeloma and myelodysplastic syndrome, lymphoma such as Hodgkin's disease and non-Hodgkin lymphoma, fibroadenoma, etc.

BRIEF DESCRIPTION OF DRAWING

FIG. 1 shows a result of evaluating anticancer effect in an endometrial cancer cell line-transplanted animal model.

DETAILED DESCRIPTION

A pharmaceutically acceptable salt of a heteroarylamine compound represented by Chemical Formula 1 according to the present invention can be prepared by a method commonly employed in the related art. The pharmaceutically acceptable salt should have low toxicity in human body and should not negatively affect the biological activity and physicochemical properties of the mother compound. A free acid that may be used to prepare the pharmaceutically acceptable salt may be either an inorganic acid or an organic acid. The inorganic acid may be hydrochloric acid, sulfuric acid, nitric acid, phosphoric acid, perchloric acid, bromic acid, etc. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc. An organic base that may be used to prepare an organic base addition salt includes tris(hydroxymethyl)methylamine, dicyclohexylamine, etc. An amino acid that may be used to prepare an amino acid addition salt includes a natural amino acid such as alanine, glycine, etc.

The heteroarylamine compound represented by Chemical Formula 1 according to the present invention includes, in addition to the above-described pharmaceutically acceptable salts, all hydrates and solvates. The hydrate and solvate may be prepared by dissolving the heteroarylamine compound represented by Chemical Formula 1 in a water-miscible solvent such as methanol, ethanol, acetone and 1,4-dioxane, and conducting crystallization or recrystallization after adding a free acid or a free base. The compound of the present invention also includes, in addition to the compounds containing various amounts of water that can be prepared, for example, through lyophilization, stoichiometric solvates including hydrates.

Hereinafter, the substituents used to define the compound according to the present invention are described in detail.

In the present invention, a 'halogen atom' refers to chloro, fluoro, bromo or iodo.

In the present invention, 'alkyl' refers to a linear, branched or cyclic aliphatic saturated hydrocarbon group having one to eight carbon atom(s), including methyl, ethyl, n-propyl, i-propyl, cyclopropyl, n-butyl, i-butyl, t-butyl, cyclobutyl, cyclopropylmethyl, n-pentyl, i-pentyl, neopentyl, t-pentyl, cyclopentyl, cyclobutylmethyl, n-hexyl, i-hexyl, cyclohexyl, cyclopentylmethyl, heptyl, cyclohexylmethyl, octyl, etc.

In the present invention, 'haloalkyl' refers to an alkyl group having one or more hydrogen atom substituted with a halogen atom, such as trifluoromethyl.

In the present invention, 'alkoxy' refers to a hydroxyl group having a hydrogen atom substituted with a $C_1$-$C_8$ alkyl group, including methoxy, ethoxy, n-propoxy, i-propoxy, n-butoxy, i-butoxy and t-butoxy.

In the present invention, 'aryl' refers to a monocyclic, bicyclic or tricyclic aromatic hydrocarbon group having six to fifteen carbon atom(s), including phenyl, naphthyl, anthryl, phenanthryl, etc.

In the present invention, 'heteroaryl' refers to a monocyclic, bicyclic or tricyclic aromatic heterohydrocarbon group containing one or more heteroatom selected from N, O and S, including pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, indolyl, isoindolyl, benzofuranyl, benzofurazanyl, dibenzofuranyl, isobenzofuranyl, indazolyl, benzimidazolyl, benzoxazolyl, benzisoxazolyl, benzothiazolyl, dibenzothiophenyl, naphthyridinyl, benzisothiazolyl, quinolinyl, isoquinolinyl, quinoxalinyl, phthalazinyl, quinolinyl, quinazolinyl, etc.

In the present invention, 'heterocycloalkyl' refers to a 5- or 6-membered aliphatic heterohydrocarbon cyclic group containing one or more heteroatom selected from N and O, including morpholinyl, piperidinyl, piperazinyl, N-protected piperazinyl, etc. In general, an N-protecting group of the piperazinyl may include an alkyl group.

Specifically, the compound represented by Chemical Formula 1 according to the present invention may be a compound wherein $X^1$, $X^2$, $X^3$ and $X^4$ are CH at the same time.

Specifically, the compound represented by Chemical Formula 1 according to the present invention may be a compound wherein $X^1$ and $X^4$ are N and $X^2$ and $X^3$ are CH.

Specifically, the compound represented by Chemical Formula 1 according to the present invention may be a compound wherein $X^1$, $X^3$ and $X^4$ are CH and $X^2$ is N.

Specifically, the compound represented by Chemical Formula 1 according to the present invention may be a compound wherein $R^1$, which is a substituent substituted at the phenyl ring, is one to four substituent(s) selected from chloro, methyl, methoxy, —NHC(O)-(3-trifluoromethylbenzene) and —C(O)NH-(3-trifluoromethylbenzene).

Specifically, the compound represented by Chemical Formula 1 according to the present invention may be a compound wherein $R^2$ is a hydrogen atom.

Specifically, the compound represented by Chemical Formula 1 according to the present invention may be a compound wherein $R^2$ is methyl, ethyl or cyclopropyl.

Specifically, the compound represented by Chemical Formula 1 according to the present invention may be a compound wherein $R^2$ is 2-(dimethylamino)ethyl or 3-(dimethylamino)propyl.

Specifically, the compound represented by Chemical Formula 1 according to the present invention may be a compound wherein $R^2$ is phenyl, methoxy-substituted phenyl, trifluoromethyl-substituted phenyl, methoxy- and methoxycarbonyl-substituted phenyl, pyridinyl, pyrimidinyl, 4-methylpiperidin-1-yl or 4-ethylpiperidin-1-yl.

Specifically, the compound represented by Chemical Formula 1 according to the present invention may be a compound wherein $R^2$ is

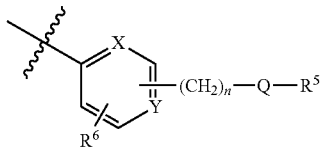

(wherein each of X and Y, which are identical to or different from each other, is CH or N, Q is piperidinyl, bipiperidinyl, piperazinyl or morpholino, $R^5$ is a hydrogen atom, methyl, ethyl, cyclohexylmethyl or methoxycarbonyl, $R^6$ is a hydrogen atom, methoxy, trifluoromethyl or methoxycarbonyl and n is an integer from 0 to 3).

Specific examples of the compound represented by Chemical Formula 1 according to the present invention are as follows:

N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine;

N-(2,6-dichloro-3,5-dimethoxyphenyl)-1-(6-((2-methoxy-(4-methylpiperazin-1-yl)phenyl)amino)pyrimidin-4-yl)-1H-benz[d]imidazol-2-amine;

N-(2,6-dichloro-3,5-dimethoxyphenyl)-1-(6-((4-morpholinophenyl)amino)pyrimidin-4-yl)-1H-benz[d]imidazol-2-amine;

N-(2,6-dichloro-3,5-dimethoxyphenyl)-1-(6-((2-methoxy-4-morpholinophenyl)amino)pyrimidin-4-yl)-1H-benz[d]imidazol-2-amine;

1-(6-((4-([1,4'-bipiperidin]-1'-yl)-3-(trifluoromethyl)phenyl)amino)pyrimidin-4-yl)-N-(2,6-dichloro-3,5-dimethoxyphenyl)-1H-benz[d]imidazol-2-amine;

1-(6-((4-((4-(cyclohexylmethyl)piperazin-1-yl)methyl)phenyl)amino)pyrimidin-4-yl)-N-(2,6-dichloro-3,5-dimethoxyphenyl)-1H-benz[d]imidazol-2-amine;

methyl 4-((6-(2-((2,6-dichloro-3,5-dimethoxyphenyl)amino)-1H-benz[d]imidazol-1-yl)pyrimidin-4-yl)amino)-3-methoxybenzoate;

1-(6-aminopyrimidin-4-yl)-N-(2,6-dichloro-3,5-dimethoxyphenyl)-1H-benz[d]imidazol-2-amine;

N-(2,6-dichloro-3,5-dimethoxyphenyl)-1-(6-(methylamino)pyrimidin-4-yl)-1H-benz[d]imidazol-2-amine;

N-(2,6-dichloro-3,5-dimethoxyphenyl)-1-(6-(phenylamino)pyrimidin-4-yl)-1H-benz[d]imidazol-2-amine;

N-(2,6-dichloro-3,5-dimethoxyphenyl)-1-(6-(pyrimidin-2-ylamino)pyrimidin-4-yl)-1H-benz[d]imidazol-2-amine;

N-(2,6-dichloro-3,5-dimethoxyphenyl)-1-(6-((6-(4-ethylpiperazin-1-yl)pyrimidin-4-yl)amino)pyrimidin-4-yl)-1H-benz[d]imidazol-2-amine;

N-(2,6-dichloro-3,5-dimethoxyphenyl)-1-(6-((1-methylpiperidin-4-yl)amino)pyrimidin-4-yl)-1H-benz[d]imidazol-2-amine;

N1-(6-(2-((2,6-dichloro-3,5-dimethoxyphenyl)amino)-1H-benz[d]imidazol-1-yl)pyrimidin-4-yl)-N2,N2-dimethylethane-1,2-diamine;

N1-(6-(2-((2,6-dichloro-3,5-dimethoxyphenyl)amino)-1H-benz[d]imidazol-1-yl)pyrimidin-4-yl)-N3,N3-dimethylpropane-1,3-diamine;

1-(6-(cyclopropylamino)pyrimidin-4-yl)-N-(2,6-dichloro-3,5-dimethoxyphenyl)-1H-benz[d]imidazol-2-amine;

N-(3,5-dimethoxyphenyl)-1-(6-((4-(4-ethylpiperazin-1-yl)phenyl)amino)pyrimidin-4-yl)-1H-benz[d]imidazol-2-amine;

N-(3,5-dimethoxyphenyl)-3-(6-((4-(4-ethylpiperazin-1-yl)phenyl)amino)pyrimidin-4-yl)-3H-imidazo[4,5-c]pyridin-2-amine;

N-(3,5-dimethoxyphenyl)-1-(6-((4-(4-ethylpiperazin-1-yl)phenyl)amino)pyrimidin-4-yl)-1H-imidazo[4,5-b]pyrazin-2-amine;

N-(3-((3-(6-((4-(4-ethylpiperazin-1-yl)phenyl)amino)pyrimidin-4-yl)-3H-imidazo[4,5-c]pyridin-2-yl)amino)-4-methylphenyl)-3-(trifluoromethyl)benzamide;

N-(3-((1-(6-((4-(4-ethylpiperazin-1-yl)phenyl)amino)pyrimidin-4-yl)-1H-imidazo[4,5-b]pyrazin-2-yl)amino)-4-methylphenyl)-3-(trifluoromethyl)benzamide; and 4-methyl-N-(3-(4-methyl-1H-imidazol-1-yl)-5-(trifluoromethyl)phenyl)-3-((3-(6-(phenylamino)pyrimidin-4-yl)-3H-imidazo[4,5-c]pyridin-2-yl)amino)benzamide.

The present invention also provides a method for preparing the compound represented by Chemical Formula 1.

The preparation method of the present invention, which is represented by Scheme 1, includes:

i) a process of preparing a compound represented by Chemical Formula 4 by coupling a compound represented by Chemical Formula 2 with a compound represented by Chemical Formula 3; and ii) a process of preparing a heteroarylamine compound represented by Chemical Formula 1 by reacting the compound represented by Chemical Formula 4 with an a amine compound represented by Chemical Formula 5 having various functional groups.

[Scheme 1]

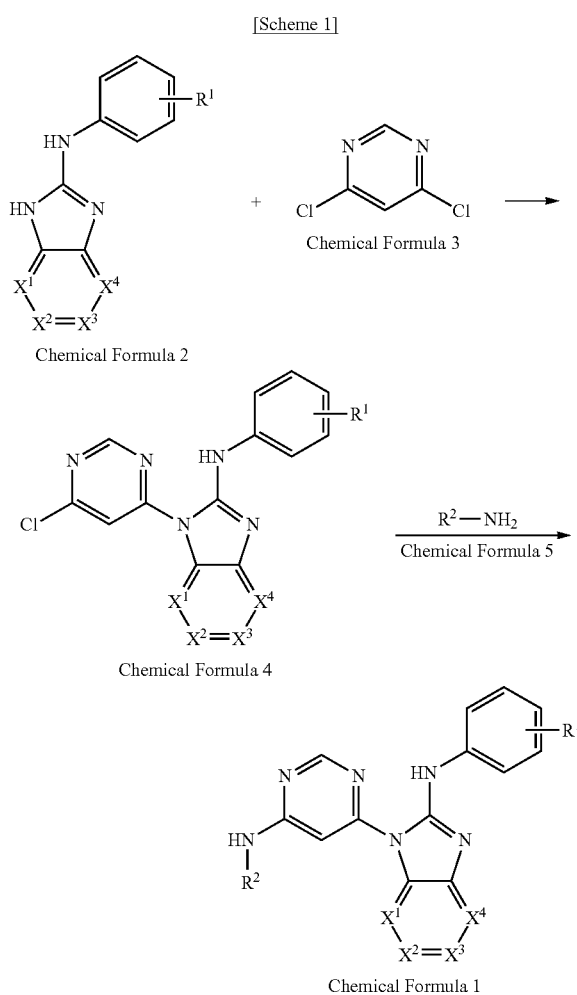

Chemical Formula 2

Chemical Formula 3

Chemical Formula 4

Chemical Formula 5

Chemical Formula 1

In Scheme 1, $X^1$, $X^2$, $X^3$, $X^4$, $R^1$ and $R^2$ are the same as defined above.

In the preparation method according to Scheme 1, the process i) is conducted by heating to 60-110° C. in the presence of an alkali metal salt as an inorganic base selected from an alkali metal hydride, an alkali metal hydroxide, etc. As a reaction solvent, a common organic solvent such as tetrahydrofuran, dioxane, N,N-dimethylformamide, N,N-dimethyl sulfoxide, 2-butanol, 2-pentanol, etc. may be used.

And, the process ii) is conducted via amination at high temperature in the presence of an acid or a base or via Buckwald amination using an organometal compound. In the Buckwald amination, $Pd_2(dba)_3$, $Pd(OAc)_2$, $PdCl_2(PPh_3)_2$, $Pd(PPh_3)_4$, etc. may be used as the metal compound. As a ligand, Xantphos (CAS number: 161265-03-8), Davephos (CAS number: 213697-53-1), Johnphos (CAS number: 224311-51-7), X-phos (CAS number: 564483-18-7), tert-Butyl Xphos (CAS number: 564483-19-8), etc. may be used. And, as the base, an amine-based organic base or a carbonate, sulfate, phosphate, alkoxide, etc. of an alkali metal or an alkaline earth metal may be used. As a reaction solvent, a common organic solvent such as tetrahydrofuran, dioxane, N,N-dimethylformamide, N,N-dimethyl sulfoxide, 2-butanol, 2-pentanol, etc. may be used. Reaction temperature may be maintained at 50-200° C., specifically 80-150° C.

The compound represented by Chemical Formula 2 and the compound represented by Chemical Formula 4, which are synthesized as reaction intermediates in the preparation method according to Scheme 1, are novel compounds first synthesized in the present invention. Accordingly, the Chemical Formula 2 or the compound represented by Chemical Formula 4 as intermediate compounds is included in the scope of the present invention.

The compound represented by Chemical Formula 2, which is used as a starting material in preparation method according to Scheme 1, may be prepared by a common organic synthesis method using an aniline derivative as a source material, as described in Scheme 2.

[Scheme 2]

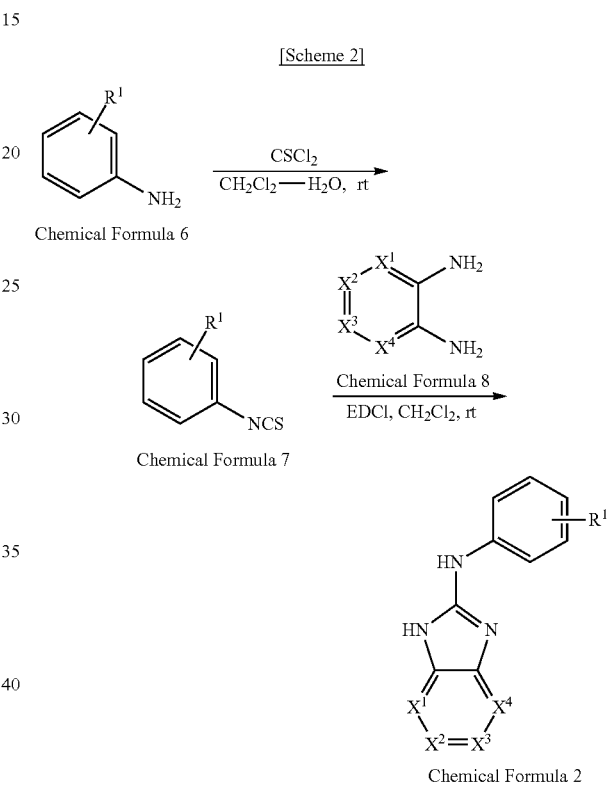

Chemical Formula 6

Chemical Formula 7

Chemical Formula 8

Chemical Formula 2

In Scheme 2, $X^1$, $X^2$, $X^3$, $X^4$ and $R^1$ are the same as defined above.

In the preparation method according to Scheme 2, first, an amine group of an aniline derivative represented by Chemical Formula 6 is converted to an isothiocyanate (NCS) group by slowly adding thiophosgene ($CSCl_2$) dropwise in a mixture solvent of dichloromethane and water. Then, a benz[d]imidazol-2-amine backbone is prepared by reacting an isothiocyanatobenzene represented by Chemical Formula 7 with a benzene-1,2-diamine represented by Chemical Formula 8. In this process, the compound represented by Chemical Formula 2 is prepared using the amidation reagent 1-ethyl-3-(3-dimethylaminopropyl)carbodiimide (EDCI) by stirring in a dichloromethane solvent.

A pharmaceutical composition containing the heteroarylamine compound represented by Chemical Formula 1, a pharmaceutically acceptable salt thereof, a solvate thereof or a hydrate thereof as an active ingredient are included in the scope of rights of the present invention.

The heteroarylamine compound represented by Chemical Formula 1 exhibits inhibition activity against various protein kinases. In particular, because it exhibits superior inhibition activity against ABL2, ACK1, ALK, BLK, BMX, c-Kit, c-Src, DDR1, DDR2, DYRK1, DYRK1B, DYRK2, EGFR, HER2, FGFR1, FGFR2, FGFR3, FGFR4, FGF, FLT3, FLT4, FMS, Fyn, Hck, MAP4K5, LCK, LIMK1, LYN, LYN B, MEKK2, MEKK3, ROS, SIK1, SIK2, SIK3, TAOK1, TAOK2, TIE2, TNK1, TRKA and YES, the pharmaceutical composition of the present invention may be used to prevent or treat a disease caused by abnormal cell growth. Specifically, the disease caused by abnormal cell growth may include various tumor diseases such as endometrial cancer, bladder cancer, stomach cancer, lung cancer, liver cancer, colon cancer, small intestine cancer, pancreatic cancer, brain cancer, bone cancer, melanoma, breast cancer, sclerosing adenosis, head and neck cancer, esophageal cancer, thyroid cancer, parathyroid cancer, kidney cancer, sarcoma, prostate cancer, urethral cancer, blood cancer such as leukemia, multiple myeloma and myelodysplastic syndrome, lymphoma such as Hodgkin's disease and non-Hodgkin lymphoma, fibroadenoma, etc.

Accordingly, the present invention provides a pharmaceutical composition containing the heteroarylamine compound represented by Chemical Formula 1, a pharmaceutically acceptable salt thereof, a solvate thereof or a hydrate thereof as an active ingredient, and an agent for preventing and treating various tumor diseases caused by abnormal cell growth.

The pharmaceutical composition of the present invention containing to one or more active ingredient selected from the heteroarylamine compound represented by Chemical Formula 1, a pharmaceutically acceptable salt thereof, a solvate and a hydrate thereof may be prepared into a formulation for oral or parenteral administration common in the pharmaceutical field, e.g., a tablet, a capsule, a troche, a liquid, a suspension, etc., by adding a commonly used nontoxic, pharmaceutically acceptable carrier, adjuvant, excipient, etc.

The excipient that may be used in the pharmaceutical composition of the present invention may include a sweetener, a binder, a solvent, a solubilizer, a wetting agent, an emulsifier, an isotonic agent, an adsorbent, a disintegrant, an antioxidant, an antiseptic, a lubricant, a filler, an aromatic, etc. Examples may include lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla flavor, etc.

An administration dosage of the compound according to the present invention to human may vary depending on the age, body weight and sex of the patient, administration type, health condition and severity of disease. A general dosage for an adult patient weighing 70 kg is 0.01-1,000 mg/day. The pharmaceutical composition may be administered once a day or several times a day with predetermined intervals at the discretion of a physician or a pharmacist.

EXAMPLES

The present invention will be described in more detail through examples, formulation examples and test examples. The following examples, formulation examples and test examples are for illustrative purposes only and it will be apparent to those skilled in the art that the scope of this invention is not limited by them.

Examples

Example 1

N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine

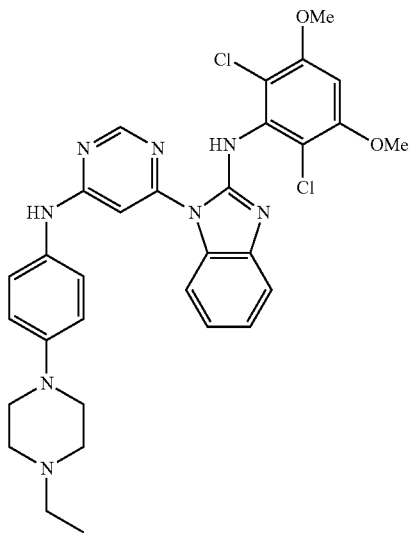 [SMILES: CCN1CCN(c2ccc(Nc3cc(-n4c(Nc5c(Cl)c(OC)cc(OC)c5Cl)nc5ccccc54)ncn3)cc2)CC1]

A compound of Example 1 having the above structural formula was prepared as follows.

Step 1: N-(3,5-dimethoxyphenyl)acetamide

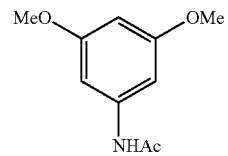 [SMILES: COc1cc(NC(C)=O)cc(OC)c1]

After slowly adding acetic anhydride (63 mL, 653.3 mmol) dropwise for 15 minutes to a solution of 3,5-dimethoxyaniline (95 g, 622.2 mmol) in toluene (500 mL), the mixture was stirred at 35-45° C. for 20 hours. The produced gray suspended matter was diluted by adding hexane (200 mL) and the produced precipitate was obtained by filtering. The resulting solid was washed with toluene/hexane (2:1, 200 mL) and hexane (100 mL) and dried to obtain a target compound (110 g, 91% yield) as a colorless solid. MS m/z: 196 [M+1]$^+$.

Step 2:
N-(2,6-dichloro-3,5-dimethoxyphenyl)acetamide

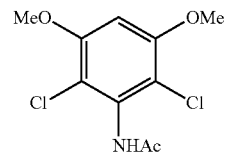

A round-bottom flask was filled with argon gas after adding N-(3,5-dimethoxyphenyl)acetamide (32.9 g, 220 mmol). After dissolving the reactant in acetonitrile (800 mL), sulfuryl chloride (SO$_2$Cl$_2$, 35 mL, 440 mmol) was slowly added at 0° C. dropwise for 15 minutes. The reaction mixture was stirred at 0° C. for 30 minutes and reaction was terminated by slowly adding a saturated sodium bicarbonate solution (500 mL) dropwise. Then, after extracting several times using ethyl acetate, the organic layer was washed with water and a saturated sodium chloride solution, dried using sodium sulfate and then concentrated. The resulting solution was purified by chromatography (ethyl acetate/hexane, 1:1→2:1) to obtain a target compound (34.5 g, 60% yield) as a colorless solid. $^1$H NMR (400 MHz, DMSO-d$_6$) δ 9.74 (s, 1H), 6.88 (s, 1H), 3.92 (s, 6H), 2.03 (s, 3H).

Step 3: 2,6-dichloro-3,5-dimethoxyaniline

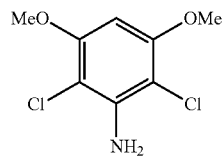

After adding a 2 N potassium hydroxide aqueous solution (400 mL) to a solution of N-(2,6-dichloro-3,5-dimethoxyphenyl)acetamide (34.5 g, 131 mmol) in ethanol (600 mL), the reaction mixture was stirred at 90° C. for 2 days under reflux. The mixture solution was cooled to room temperature and stirred again for 1 hour after cooling to 0° C. using ice water. The produced solid was filtered, washed with a cold ethanol/water (1:1) mixture solvent and then dried to obtain a target compound (22.1 g, 76% yield). $^1$H NMR (400 MHz, DMSO-d$_6$) δ 6.21 (s, 1H), 5.40 (s, 2H), 3.83 (s, 6H).

Step 4: 2,4-dichloro-3-isothiocyanato-1,5-dimethoxybenzene

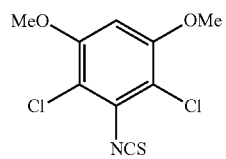

After adding 2,6-dichloro-3,5-dimethoxyaniline (10.1 g, 45 mmol) to a mixture solvent of dichloromethane (80 mL) and water (30 mL) and slowly adding thiophosgene (10 mL) dropwise for 20 minutes, the reaction mixture was stirred for 2 days. Then, after extracting several times using dichloromethane, the organic layer was washed with water and a saturated sodium chloride solution, dried using sodium sulfate and then concentrated to obtain a target compound (13.5 g) as a yellow solid.

Step 5: N-(2,6-dichloro-3,5-dimethoxyphenyl)-1H-benz[d]imidazol-3-amine

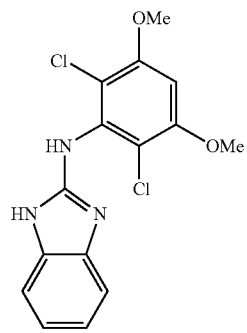 [SMILES: COc1cc(OC)c(Cl)c(Nc2nc3ccccc3[nH]2)c1Cl]

After adding a solution of the 2,4-dichloro-3-isothiocyanato-1,5-dimethoxybenzene (13.5 g, 45 mmol) obtained in the step 4 in dichloromethane (150 mL) to benzene-1,2-diamine (9.7 g, 90 mmol), the mixture was stirred for 12 hours. Then, after adding EDCI (17.3 g, 90 mmol), the reaction mixture was further stirred for 12 hours. The reaction mixture was concentrated without special purification and then purified by column chromatography (ethyl acetate/hexane, 1:1→dichloromethane/methanol, 10:1) to obtain a target compound (10 g, 66% yield) as a yellow solid. $^1$H NMR (400 MHz, DMSO-d$_6$) δ 12.10 (brs, 1H), 7.30 (m, 2H), 7.20 (m, 2H), 7.06 (s, 1H), 3.99 (s, 6H). MS m/z: 338 [M+1]$^+$.

Step 6: 1-(6-chloropyrimidin-4-yl)-N-(2,6-dichloro-3,5-dimethoxyphenyl)-1H-benz[d]imidazol-2-amine

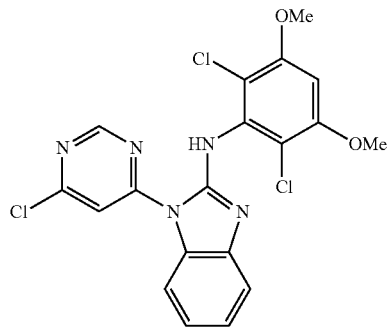 [SMILES: COc1cc(OC)c(Cl)c(Nc2nc3ccccc3n2-c2cc(Cl)ncn2)c1Cl]

N-(2,6-Dichloro-3,5-dimethoxyphenyl)-1H-benz[d]imidazol-3-amine (45 mg, 0.108 mmol) and 4,6-dichloropyrimidine (40 mg, 0.27 mmol) were dissolved in dimethyl sulfoxide (DMSO, 0.4 mL) and the mixture was cooled to 0° C. After slowly adding 60% sodium hydride (6.6 mg, 0.165 mmol) and heating to 90° C., the mixture was stirred for 3 hours. Then, after cooling to room temperature, reaction was terminated by adding water. After extracting several times using ethyl acetate, the resulting organic layer was washed with water and a saturated sodium chloride solution, dried using sodium sulfate and then concentrated. The obtained residue was washed four times with acetonitrile (8 mL) and the solvent was removed to obtain a target compound (24 mg, 42% yield). $^1$H NMR (400 MHz, DMSO-$d_6$) δ 10.97 (brs, 1H) 9.07 (s, 1H), 8.99 (s, 1H), 8.33 (d, J=7.6 Hz, 1H), 7.14 (m, 1H) 7.08 (m, 1H), 6.98 (d, J=8 Hz, 1H), 6.70 (s, 1H), 3.93 (s, 6H). MS m/z: 451 [M+1]$^+$.

Step 7: N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine

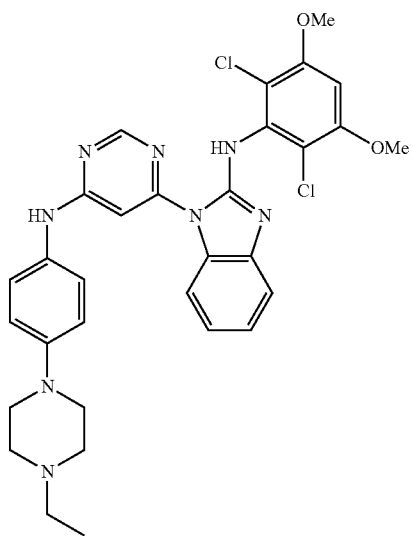 [SMILES: CCN1CCN(c2ccc(Nc3cc(-n4c(Nc5c(Cl)c(OC)cc(OC)c5Cl)nc5ccccc54)ncn3)cc2)CC1]

After dissolving 1-(6-chloropyrimidin-4-yl)-N-(2,6-dichloro-3,5-dimethoxyphenyl)-1H-benz[d]imidazol-2-amine (20 mg, 0.044 mmol) and 4-(4-ethylpiperazin-1-yl)aniline (13.6 mg, 0.066 mmol) in a mixture of 1,4-dioxane (0.1 mL) and dimethyl sulfoxide (0.1 mL) and cooling to 0° C., trifluoroacetic acid (10.2 μL, 0.133 mmol) was slowly added dropwise. Then, after heating to 120° C., the reaction mixture was stirred for 20 hours. After the reaction was terminated, the reaction mixture was cooled to room temperature. After extracting several times using ethyl acetate, the obtained organic layer was washed with water and a saturated sodium chloride solution, dried using sodium sulfate and then concentrated. The obtained residue was purified by column chromatography (dichloromethane/methanol, 20:1) to obtain a target compound (16 mg, 59% yield) as a yellow solid. $^1$H NMR (400 MHz, CDCl$_3$) δ 9.91 (brs, 1H), 8.62 (s, 1H), 7.49 (d, J=7.6 Hz, 1H), 7.28H (m, 2H), 7.15 (t, J=7.6 Hz, 2H), 7.02 (t, J=8.0 Hz, 1H), 7.00 (d, J=8.8 Hz, 2H), 6.51 (s, 1H), 3.93 (s, 6H), 3.26 (t, J=4.6 Hz, 4H), 2.64 (t, J=4.4 Hz, 4H), 2.36 (q, J=7.2 Hz, 2H), 1.15 (t, J=7.2 Hz, 3H). $^{13}$C NMR (400 MHz, CDCl$_3$) δ 163.49, 158.07, 156.36, 154.72, 150.63, 149.39, 142.67, 135.44, 131.39, 129.12, 124.81, 123.28, 120.86, 117.78, 116.76, 112.85, 110.17, 95.25, 92.88, 56.47, 52.64, 52.30, 49.03, 11.85. MS m/z: 620 [M+1]$^+$.

Example 2

N-(2,6-dichloro-3,5-dimethoxyphenyl)-1-(6-((2-methoxy-4-(4-methylpiperazin-1-yl)phenyl)amino)pyrimidin-4-yl)-1H-benz[d]imidazol-2-amine

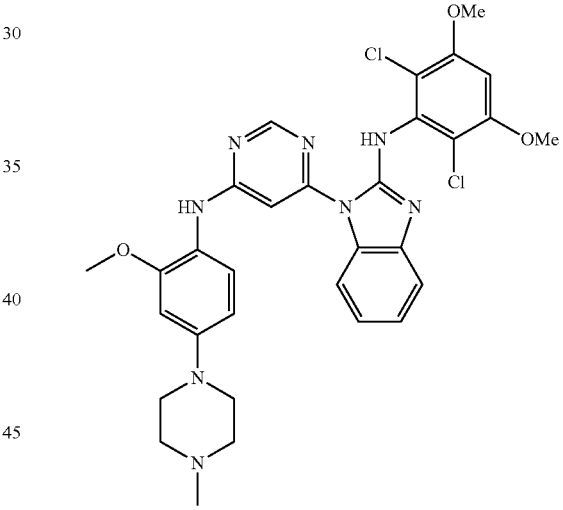

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and 2-methoxy-4-(4-methylpiperazin-1-yl)aniline. $^1$H NMR (400 MHz, CDCl$_3$) δ 9.87 (brs, 1H), 8.65 (d, J=0.4 Hz, 1H), 7.56 (brs, 1H), 7.50 (d, J=6.8 Hz, 1H), 7.37 (d, J=8.0 Hz, 1H), 7.16 (t, J=7.6 Hz, 1H), 7.09-7.04 (m, 2H), 6.88 (brs, 1H), 6.57 (m, 2H), 6.52 (s, 1H), 3.93 (s, 6H), 3.89 (s, 3H), 3.29 (t, J=4.4 Hz, 4H), 2.70 (brs, 4H), 2.44 (s, 3H). $^{13}$C NMR (400 MHz, CDCl$_3$) δ 163.14, 158.15, 156.50, 154.78, 150.39, 142.97, 135.57, 131.54, 124.66, 123.26, 120.76, 118.84, 118.21, 112.80, 110.05, 108.22, 100.49, 95.31, 93.32, 56.56, 55.64, 54.78, 49.03, 45.71. MS m/z: 635 [M+1]$^+$.

Example 3

N-(2,6-dichloro-3,5-dimethoxyphenyl)-1-(6-((4-morpholinophenyl)amino)pyrimidin-4-yl)-1H-benz[d]imidazol-2-amine

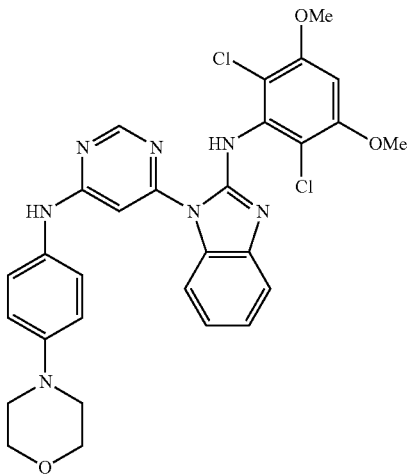 [SMILES: COc1cc(OC)c(Cl)c(Nc2nc3ccccc3n2-c2cc(Nc3ccc(N4CCOCC4)cc3)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and 4-morpholinoaniline $^1$H NMR (400 MHz, CDCl$_3$) 9.95 (brs, 1H), 8.62 (d, J=0.4 Hz, 1H), 7.47 (brs, 2H), 7.32 (d, J=8.4 Hz, 3H), 7.14 (t, J=7.4 Hz, 1H), 7.03 (t, J=7.6 Hz, 1H), 6.97 (d, J=8.8 Hz, 2H), 6.91 (brs, 1H), 6.49 (s, 1H), 3.91 (s, 6H), 3.89 (t, J=4.8 Hz, 4H), 3.18 (t, J=4.4 Hz, 4H). $^{13}$C NMR (400 MHz, CDCl$_3$) 163.51, 158.18, 456.49, 154.82, 149.59, 135.32, 131.21, 129.24, 128.78, 125.21, 123.44, 121.06, 117.94, 116.58, 112.77, 110.21, 66.78, 56.55, 49.34. MS m/z: 593 [M+1]$^+$.

Example 4

N-(2,6-dichloro-3,5-dimethoxyphenyl)-1-(6-((2-methoxy-4-morpholinophenyl)amino)pyrimidin-4-yl)-1H-benz[d]imidazol-2-amine

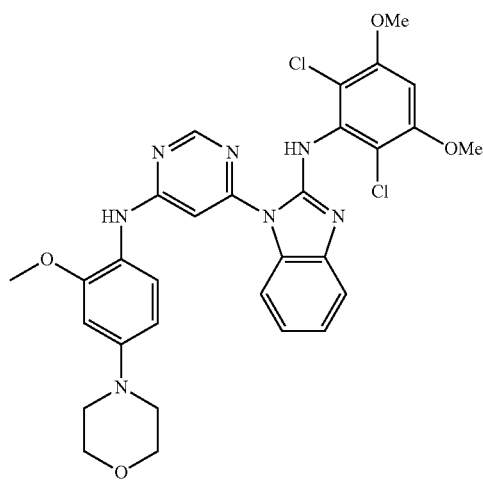 [SMILES: COc1cc(N2CCOCC2)ccc1Nc1cc(-n2c(Nc3c(Cl)c(OC)cc(OC)c3Cl)nc3ccccc32)ncn1]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and 2-methoxy-4-morpholinoaniline $^1$H NMR (400 MHz, CDCl$_3$) 9.90 (brs, 1H), 8.65 (d, J=0.8 Hz, 1H), 7.58 (brs, 1H), 7.52 (brs, 1H), 7.38 (brs, 1H), 7.17 (t, J=7.4 Hz, 1H), 7.12 (brs, 1H), 7.09-0.05 (m, 1H), 6.88 (brs, 1H), 6.56 (m, 2H), 6.52 (s, 1H), 3.93 (s, 6H), 3.89 (t, J=4.8 Hz, 3H), 3.89 (s, 3H), 3.19 (t, J=4.8 Hz, 4H). MS m/z: 622 [M+1]$^+$.

Example 5

1-(6-((4-([1,4'-bipiperidin]-1'-yl)-3-(trifluoromethyl)phenyl)amino)pyrimidin-4-yl)-N-(2,6-dichloro-3,5-dimethoxyphenyl)-1H-benz[d]imidazol-2-amine

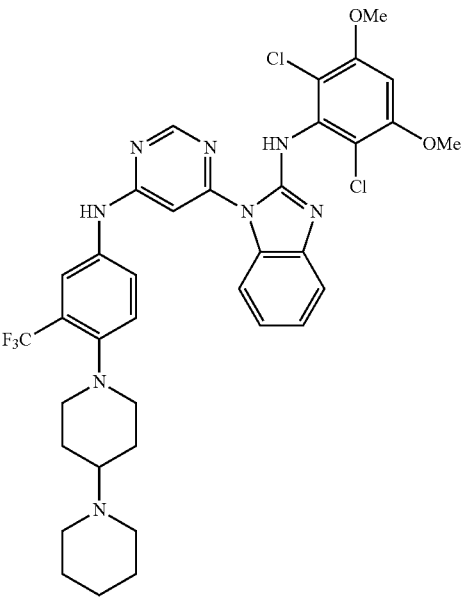 [SMILES: COc1cc(OC)c(Cl)c(Nc2nc3ccccc3n2-c2cc(Nc3ccc(N4CCC(N5CCCCC5)CC4)c(C(F)(F)F)c3)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and 4-([1,4'-bipiperidin]-1'-yl)-3-(trifluoromethyl)aniline $^1$H NMR (400 MHz, CDCl$_3$) δ 11.65 (s, 1H), 9.90 (brs, 1H), 8.69 (s, 1H), 8.05 (s, 1H), 7.77 (d, J=7.6 Hz, 1H), 7.65 (brs, 1H), 7.48 (brs, 1H), 7.41 (brs, 1H), 7.22 (d, J=8.8 Hz, 1H), 7.15 (t, J=7.4 Hz, 1H), 7.08 (t, J=7.8 Hz, 1H), 6.47 (s, 1H), 3.89 (s, 6H), 3.26 (d, J=10.8 Hz, 2H), 3.13 (t, J=10.0 Hz, 1H), 3.00 (d, J=10.4 Hz, 2H), 2.76 (q, J=11.07 Hz, 2H), 2.66 (t, J=11.0 Hz, 2H), 2.37 (q, J=12.53 Hz, 2H), 2.25 (d, J=10.0 Hz, 2H), 1.87 (m, 5H), 1.35 (q, J=12.8 Hz, 1H). MS m/z: 741 [M+1]$^+$.

Example 6

1-(6-((4-((4-(cyclohexylmethyl)piperazin-1-yl)methyl)phenyl)amino)pyrimidin-4-yl)-N-(2,6-dichloro-3,5-dimethoxyphenyl)-1H-benz[d]imidazol-2-amine

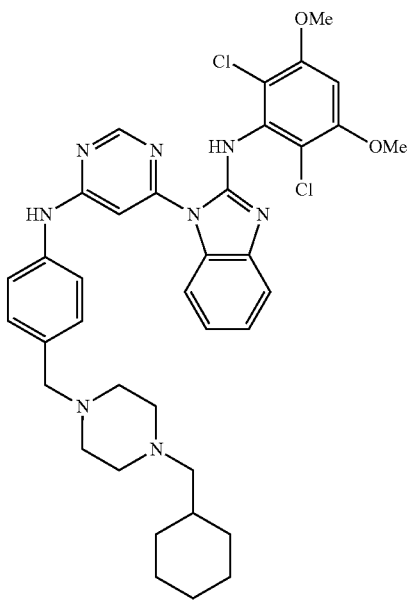 [SMILES: COc1cc(OC)c(Cl)c(Nc2nc3ccccc3n2-c2cc(Nc3ccc(CN4CCN(CC5CCCCC5)CC4)cc3)ncn2)c1Cl]

1-(6-Chloropyrimidin-4-yl)-N-(2,6-dichloro-3,5-dimethoxyphenyl)-1H-benz[d]imidazol-2-amine and 4-((4-(cyclohexylmethyl)piperazin-1-yl)methyl)aniline were dissolved in a mixture of 1,4-dioxane and dimethyl sulfoxide. After adding tBu-XPhos and potassium carbonate, gas was removed for 5 minutes using an ultrasound sonicator. Then, after adding $Pd_2(dba)_3$, the mixture was stirred at 120° C. for 20 hours. After the reaction was completed, the mixture was cooled to room temperature and the solid residue was filtered. After extracting several times using ethyl acetate, the obtained organic layer was washed with water and a saturated sodium chloride solution, dried using sodium sulfate and then concentrated. The obtained residue was purified by column chromatography to obtain a target compound. MS m/z: 702 [M+1]+.

Example 7 methyl 4-((6-(2-((2,6-dichloro-3,5-dimethoxyphenyl)amino)-1H-benz[d]imidazol-1-yl)pyrimidin-1-yl)amino)-3-methoxybenzoate

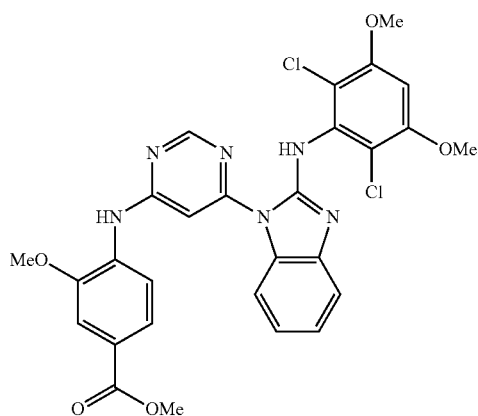 [SMILES: COC(=O)c1ccc(Nc2cc(-n3c(Nc4c(Cl)c(OC)cc(OC)c4Cl)nc4ccccc43)ncn2)c(OC)c1]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and methyl 4-amino-3-methoxybenzoate. $^1$H NMR (400 MHz, $CDCl_3$) δ 9.94 (brs, 1H), 8.80 (s, 1H), 8.37 (d, J=8.4 Hz 1H), 7.76 (d, J=8.4 Hz, 1H), 7.63 (s, 1H), 7.59 (brs, 2H), 7.22 (t, J=7.6 Hz, 1H), 7.16 (t, J=7.6 Hz, 1H), 6.51 (s, 1H), 4.01 (s, 3H), 3.93 (s, 3H), 3.93 (s, 6H). MS m/z: 595 [M+1]+.

Example 8

1-(6-aminopyrimidin-1-yl)-N-(2,6-dichloro-3,5-dimethoxyphenyl)-1H-benz[d]imidazol-2-amine

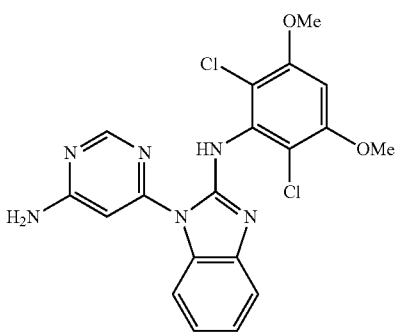 [SMILES: COc1cc(OC)c(Cl)c(Nc2nc3ccccc3n2-c2cc(N)ncn2)c1Cl]

1-(6-Chloropyrimidin-4-yl)-N-(2,6-dichloro-3,5-dimethoxyphenyl)-1H-benz[d]imidazol-2-amine and ammonium chloride were dissolved in a mixture of 1,4-dioxane and dimethyl sulfoxide. After adding diisopropylethylamine, the mixture was stirred at 120° C. for 20 hours. After the reaction was completed, the mixture was cooled to room temperature and extracted several times using ethyl acetate. The obtained organic layer was washed with water and a saturated sodium chloride solution, dried using sodium sulfate and then concentrated. The obtained residue was purified by column chromatography to obtain a target compound. $^1$H NMR (400 MHz, $CDCl_3$) δ 9.80 (brs, 1H), 8.58 (d, J=0.8 1H), 7.53 (brs, 1H), 7.47 (brs, 1H), 7.17 (t, J=7.2 Hz, 1H), 7.10 (m, 1H), 6.89 (brs, 1H), 6.51 (s, 1H), 5.42 (s, 2H), 3.93 (s, 6H). MS m/z: 431 [M+1]+.

Example 9

N-(2,6-dichloro-3,5-dimethoxyphenyl)-1-(6-(methylamino)pyrimidin-4-yl)-1H-benz[d]imidazol-2-amine

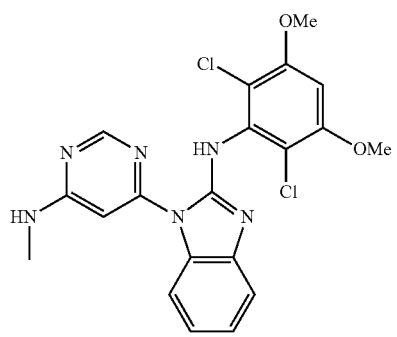 [SMILES: CNc1cc(-n2c(Nc3c(Cl)c(OC)cc(OC)c3Cl)nc3ccccc32)ncn1]

A target compound was obtained in the same manner as Example 8 using 1-(6-chloropyrimidin-4-yl)-N-(2,6-dichloro-3,5-dimethoxyphenyl)-1H-benz[d]imidazol-2-amine and methylamine hydrochloride. $^1$NMR (400 MHz, CDCl$_3$) δ 9.99 (brs, 1H), 8.56 (s, 1H), 7.52 (brs, 1H), 7.49 (brs, 1H), 7.17 (t, J=7.4 Hz, 1H), 7.09 (t, J=7.4 Hz, 1H), 6.70 (brs, 1H), 6.49 (s, 1H), 5.73 (brs, 1H), 3.91 (s, 6H), 3.03 (d, J=5.2 Hz, 3H). MS m/z: 445 [M+1]$^+$.

Example 10

N-(2,6-dichloro-3,5-dimethoxyphenyl)-1-(6-(phenylamino)pyrimidin-4-yl)-1H-benz[d]imidazol-2-amine

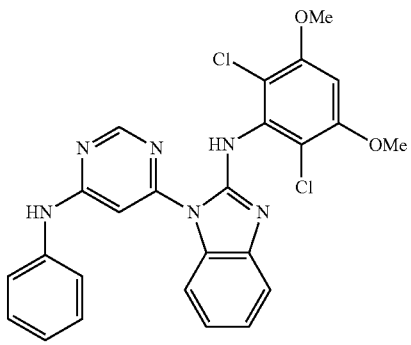 [SMILES: COc1cc(OC)c(Cl)c(Nc2nc3ccccc3n2-c2cc(Nc3ccccc3)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and aniline $^1$H NMR (400 MHz, CDCl$_3$) δ 9.94 (brs, 1H), 8.67 (d, J=0.4 Hz, 1H), 7.76 (brs, 1H), 7.44 (m, 5H), 7.33 (brs, 1H), 7.23 (brs, 1H), 7.13 (t, J=7.6 Hz, 1H), 7.00 (brs, 1H), 6.98 (t, J=7.8 Hz, 1H), 6.45 (s, 1H), 3.88 (s, 6H). MS m/z: 508 [M+1]$^+$.

Example 11

N-(2,6-dichloro-3,5-dimethoxyphenyl)-1-(6-(pyrimidin-2-ylamino)pyrimidin-4-yl)-1H-benz[d]imidazol-2-amine

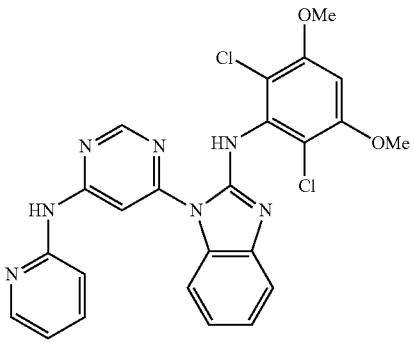 [SMILES: COc1cc(OC)c(Cl)c(Nc2nc3ccccc3n2-c2cc(Nc3ccccn3)ncn2)c1Cl]

1-(6-Chloropyrimidin-4-yl)-N-(2,6-dichloro-3,5-dimethoxyphenyl)-1H-benz[d]imidazol-2-amine and 2-aminopyridine were dissolved in a mixture of 1,4-dioxane and dimethyl sulfoxide. After adding BINAP and potassium carbonate, gas was removed for 5 minutes using an ultrasound sonicator. Then, after adding Pd(OAc)$_2$, the mixture was stirred at 120° C. for 20 hours. After the reaction was completed, the mixture was cooled to room temperature and the solid residue was filtered. After extracting several times using ethyl acetate, the obtained organic layer was washed with water and a saturated sodium chloride solution, dried using sodium sulfate and then concentrated. The obtained residue was purified by column chromatography to obtain a target compound. MS m/z: 509 [M+1]$^+$.

Example 12

N-(2,6-dichloro-3,5-dimethoxyphenyl)-1-(6-((6-(4-ethylpiperazin-1-yl)pyrimidin-4-yl)amino)pyrimidin-4-yl)-1H-benz[d]imidazol-2-amine

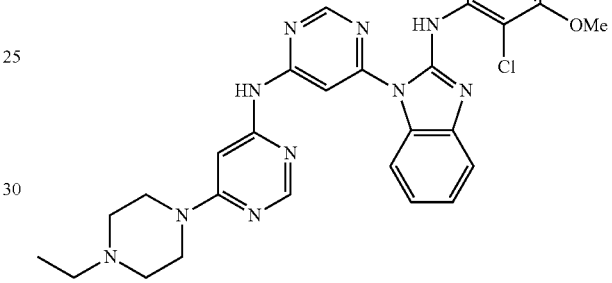

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and 6-(4-ethylpiperazin-1-yl)pyrimidin-4-amine. MS m/z: 622 [M+1]$^+$.

Example 13

N-(2,6-dichloro-3,5-dimethoxyphenyl)-1-(6-((1-methylpiperidin-4-yl)amino)pyrimidin-4-yl)-1H-benz[d]imidazol-2-amine

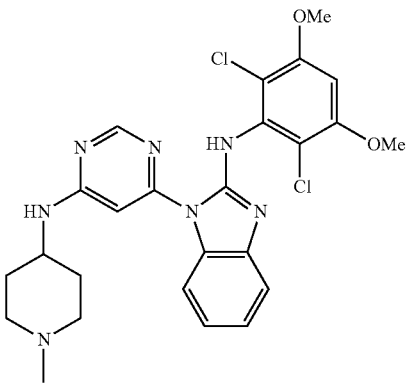 [SMILES: COc1cc(OC)c(Cl)c(Nc2nc3ccccc3n2-c2cc(NC3CCN(C)CC3)ncn2)c1Cl]

A target compound was obtained in the same manner as the step 7 of Example 1 using 1-(6-chloropyrimidin-4-yl)-

N-(2,6-dichloro-3,5-dimethoxyphenyl)-1H-benz[d]imidazol-2-amine and 1-methylpiperidin-4-amine. MS m/z: 528 [M+1]⁺.

Example 14

N1-(6-(2-((2,6-dichloro-3,5-dimethoxyphenyl)amino)-1H-benz[d]imidazol-1-yl)pyrimidin-4-yl)-N2,N2-dimethylethane-1,2-diamine

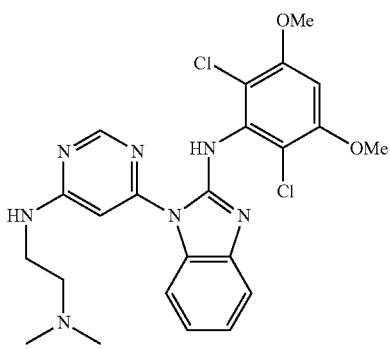 [SMILES: COc1cc(OC)c(Cl)c(Nc2nc3ccccc3n2-c2cc(NCCN(C)C)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and N,N-dimethylethane-1,2-diamine. MS m/z: 502 [M+1]⁺.

Example 15

N1-(6-(2-((2,6-dichloro-3,5-dimethoxyphenyl)amino)-1H-benz[d]imidazol-1-yl)pyrimidin-4-yl)-N3,N3-dimethylpropane-1,3-diamine

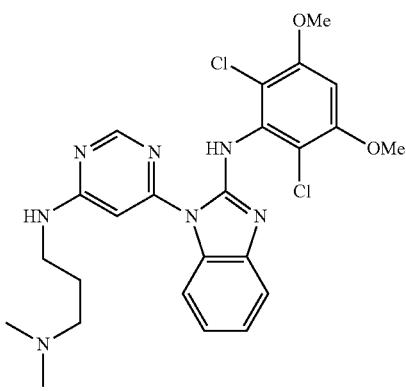 [SMILES: COc1cc(OC)c(Cl)c(Nc2nc3ccccc3n2-c2cc(NCCCN(C)C)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and N,N-dimethylpropane-1,3-diamine. MS m/z: 516 [M+1]⁺.

Example 16

1-(6-(cyclopropylamino)pyrimidin-4-yl)-N-(2,6-dichloro-3,5-dimethoxyphenyl)-1H-benz[d]imidazol-2-amine

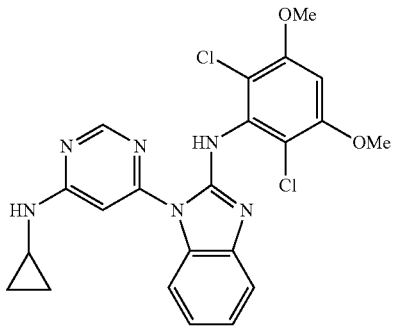 [SMILES: COc1cc(OC)c(Cl)c(Nc2nc3ccccc3n2-c2cc(NC3CC3)ncn2)c1Cl]

A target compound was obtained in the same manner as the step 7 of Example 1 using 1-(6-chloropyrimidin-4-yl)-N-(2,6-dichloro-3,5-dimethoxyphenyl)-1H-benz[d]imidazol-2-amine and cyclopropylamine. MS m/z: 471 [M+1]⁺.

Example 17

N-(3,5-dimethoxyphenyl)-1-(6-((4-(4-ethylpiperazin-1-yl)phenyl)amino)pyrimidin-4-yl)-1H-benz[d]imidazol-2-amine

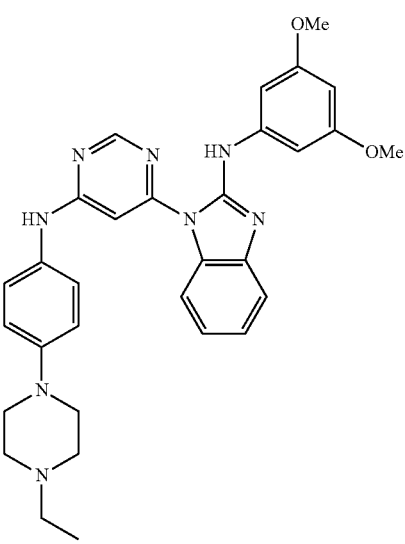 [SMILES: CCN1CCN(c2ccc(Nc3cc(-n4c(Nc5cc(OC)cc(OC)c5)nc5ccccc54)ncn3)cc2)CC1]

A target compound was obtained in the same manner as the step 7 of Example 1 using 1-(6-chloropyrimidin-4-yl)-N-(3,5-dimethoxyphenyl)-1H-benz[d]imidazol-2-amine and (4-ethylpiperazin-1-yl)phenylamine. MS m/z: 551.67 [M+1]⁺.

Example 18

N-(3,5-dimethoxyphenyl)-3-(6-((4-(4-ethylpiperazin-1-yl)phenyl)amino)pyrimidin-4-yl)-3H-imidazo[4,5-c]pyridin-2-amine

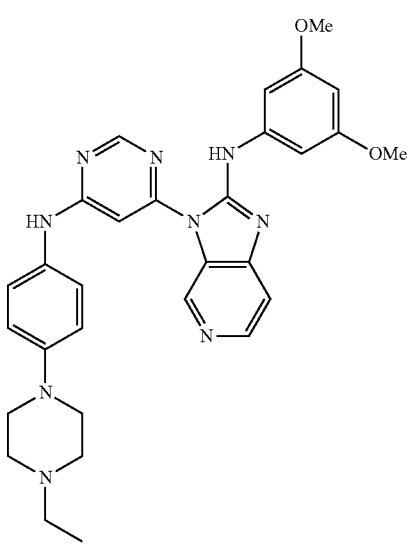 [SMILES: CCN1CCN(c2ccc(Nc3cc(-n4c(Nc5cc(OC)cc(OC)c5)nc5ccncc54)ncn3)cc2)CC1]

A target compound was obtained in the same manner as the step 7 of Example 1 using 3-(6-chloropyrimidin-4-yl)-N-(3,5-dimethoxyphenyl)-3H-imidazo[4,5-c]pyridin-2-amine and (4-ethylpiperazin-1-yl)phenylamine. MS m/z: 552.66 [M+1]$^+$.

Example 19

N-(3,5-dimethoxyphenyl)-1-(6-((4-(4-ethylpiperazin-1-yl)phenyl)amino)pyrimidin-4-yl)-1H-imidazo[4,5-b]pyrazin-2-amine

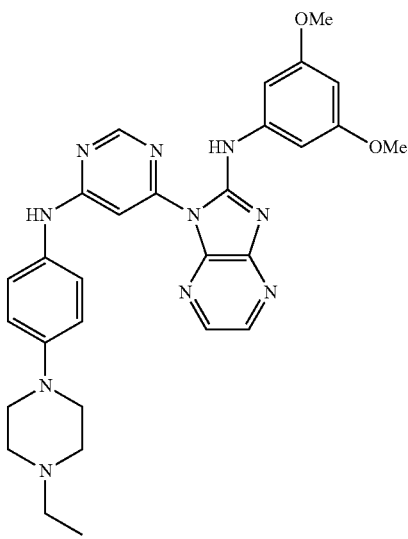 [SMILES: CCN1CCN(c2ccc(Nc3cc(-n4c(Nc5cc(OC)cc(OC)c5)nc5nccnc54)ncn3)cc2)CC1]

A target compound was obtained in the same manner as the step 7 of Example 1 using 1-(6-chloropyrimidin-4-yl)-N-(3,5-dimethoxyphenyl)-1H-imidazo[4,5-b]pyrazin-2-amine and (4-ethylpiperazin-1-yl)phenylamine. MS m/z: 553.64 [M+1]$^+$.

Example 20

N-(3-((3-(6-((4-(4-ethylpiperazin-1-yl)phenyl)amino)pyrimidin-4-yl)-3H-imidazo[4,5-c]pyridin-2-yl)amino)-4-methylphenyl)-3-(trifluoromethyl)benzamide

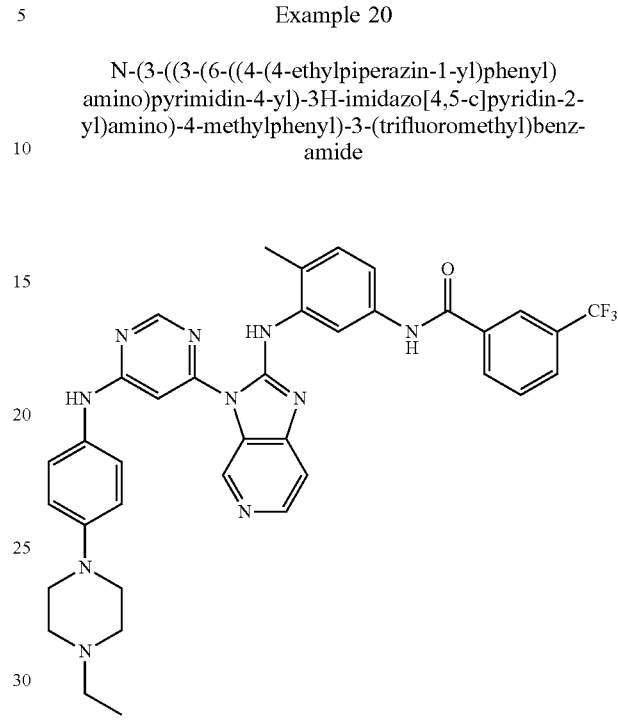

A target compound was obtained in the same manner as the step 7 of Example 1 using N-(3-((3-(6-chloropyridin-4-yl)-3H-imidazo[4,5-c]pyridin-2-yl)amino)-4-methylphenyl)-3-(trifluoromethyl)benzamide and (4-ethylpiperazin-1-yl)phenylamine. MS m/z: 693.75 [M+1]$^+$.

Example 21

N-(3-((1-(6-((4-(4-ethylpiperazin-1-yl)phenyl)amino)pyrimidin-4-yl)-1H-imidazo[4,5-b]pyrazin-2-yl)amino)-4-methylphenyl)-3-(trifluoromethyl)benzamide

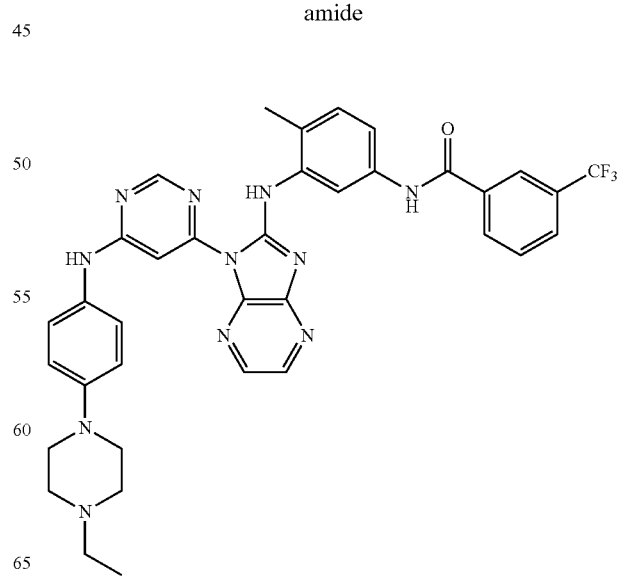

A target compound was obtained in the same manner as the step 7 of Example 1 using N-(3-((1-(6-chloropyridin-4-yl)-1H-imidazo[4,5-b]pyrazin-2-yl)amino)-4-methylphenyl)-3-(trifluoromethyl)benzamide and (4-ethylpiperazin-1-yl)phenylamine. MS m/z: 694.74 [M+1]$^+$.

Example 22

4-methyl-N-(3-(4-methyl-1H-imidazol-1-yl)-5-(trifluoromethyl)phenyl)-3-((3-(6-(phenylamino)pyrimidin-4-yl)-3H-imidazo[4,5-c]pyridin-2-yl)amino) benzamide

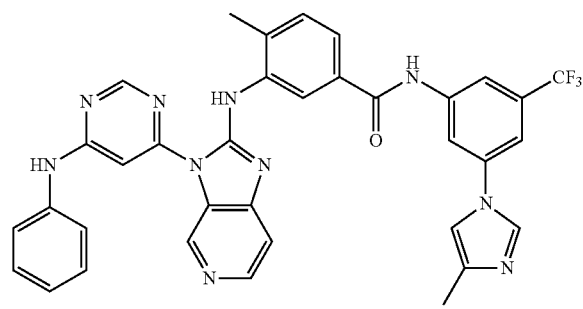 [SMILES: Cc1cn(-c2cc(NC(=O)c3ccc(C)c(Nc4nc5ccncc5n4-c4cc(Nc5ccccc5)ncn4)c3)cc(C(F)(F)F)c2)cn1]

A target compound was obtained in the same manner as the step 7 of Example 1 using 3-((3-(6-chloropyrimidin-4-yl)-3H-imidazo[4,5-c]pyridin-2-yl)amino)-4-methyl-N-(3-(4-methyl-1H-imidazol-1-yl)-5-(trifluoromethyl)phenyl) benzamide and aniline MS m/z: 661.67 [M+1]$^+$.

The novel compound represented by Chemical Formula 1 according to the present invention can be prepared into various formulations depending on purposes. Some formulation examples containing the compound represented by Chemical Formula 1 according to the present invention as an active ingredient are described below. However, the present invention is not limited by them.

FORMULATION EXAMPLES

Formulation Example 1

Tablet (Direct Compression)

5.0 mg of the active ingredient was sieved, mixed with 14.1 mg of lactose, 0.8 mg of crospovidone USNF and 0.1 mg of magnesium stearate and then compressed into a tablet.

Formulation Example 2

Tablet (Wet Granulation)

5.0 mg of the active ingredient was sieved and mixed with 16.0 mg of lactose and 4.0 mg of starch. After adding a solution of 0.3 mg of polysorbate 80 in pure water, the mixture was prepared into a granule. After drying, the granule was sieved and mixed with 2.7 mg of colloidal silicon dioxide and 2.0 mg of magnesium stearate. The granule was compressed into a tablet.

Formulation Example 3

Powder and Capsule 5.0 mg of the active ingredient was sieved and mixed with 14.8 mg of lactose, 10.0 mg of polyvinylpyrrolidone and 0.2 mg of magnesium stearate. The mixture was filled in a No. 5 gelatin capsule using an adequate apparatus.

Formulation Example 4

Injection

An injection was prepared using 100 mg of the active ingredient, 180 mg of mannitol, 26 mg of $Na_2HPO_4.12H_2O$ and 2974 mg of distilled water.

Test Examples

Test Example 1

Measurement of Kinase Inhibition Activity

In order to measure the inhibition activity (% inhibition) of the compound of the present invention against protein kinases, a biochemical assay was conducted using a full kinase panel consisting of 340 kinases. As a representative compound of the present invention, N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1 was used.

The kinases whose activity is inhibited by 50% or more when treated with 1 μM of the compound of Example 1 are listed in Table 1.

TABLE 1

| Kinases whose activity is inhibited by 50% or more | |
|---|---|
| ABL2 | ACK1 |
| ALK | BLK |
| BMX | c-Kit |
| c-Src | DDR1 |
| DDR2 | DYRK1 |
| DYRK1B | DYRK2 |
| EGFR | HER2 |
| FGFR1 | FGFR2 |
| FGFR3 | FGFR4 |
| FGF | FLT3 |
| FLT4 | FMS |
| Fyn | Hck |
| MAP4K5 | LCK |
| LIMK1 | LYN |
| LYN B | MEKK2 |
| MEKK3 | ROS |
| SIK1 | SIK2 |
| SIK3 | TAOK1 |
| TAOK2 | TIE2 |
| TNK1 | TRKA |
| YES | |

Test Example 2

Evaluation of Ability of Inhibiting Proliferation of Cancer Cells

The ability of the compound of the present invention of inhibiting the proliferation of the bladder cancer cell line RT112 was determined as the $GI_{50}$ value. The result is shown in Table 2.

TABLE 2

| Compounds | Ability of inhibiting proliferation of RT112 ($GI_{50}$, μM) |
|---|---|
| Compound of Example 1 | <1 |
| Compound of Example 2 | <1 |

TABLE 2-continued

| Compounds | Ability of inhibiting proliferation of RT112 (GI$_{50}$, μM) |
|---|---|
| Compound of Example 3 | <1 |
| Compound of Example 4 | <1 |
| Compound of Example 5 | <10 |
| Compound of Example 6 | <10 |
| Compound of Example 8 | <1 |
| Compound of Example 9 | <1 |
| Compound of Example 10 | <1 |
| Compound of Example 11 | <1 |

Test Example 4

Evaluation of Inhibition Activity Against CYPs (Cytochromes P450)

The inhibition activity (inhibition rate, %) of N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1, as a representative compound of the present invention, against CYPs (cytochromes P450) was measured in order to investigate the risk of drug side effects. The result is shown in Table 5. It can be seen that the compound of the present invention exhibits no inhibition activity against the five CYPs: CYP1A2, CYP2C9, CYP2C19, CYP2D6 and CYP3A4.

TABLE 5

| | Concentration (μM) | CYPs | | | | |
|---|---|---|---|---|---|---|
| | | CYP1A2 | CYP2C9 | CYP2C19 | CYP2D6 | CYP3A4 |
| % inhibition | 0 | 0.00 | 0.00 | 0.00 | 0.00 | 0.00 |
| | 0.1 | 5.36 | 10.26 | 2.72 | −3.15 | 3.09 |
| | 0.5 | 4.67 | 8.79 | 3.23 | −4.76 | 3.70 |
| | 5 | −1.90 | 24.59 | 30.01 | −2.56 | 24.44 |
| | 10 | −3.46 | 29.97 | 37.26 | 6.12 | 31.82 |
| | 25 | −3.11 | 52.41 | 66.07 | 13.61 | 49.66 |
| | 50 | 2.08 | 53.37 | 67.96 | 13.38 | 55.49 |
| | Positive control | 52.04 | 95.56 | 89.08 | 97.07 | 88.98 |
| | Expected IC$_{50}$ | >50 | 44.82 | 16.64 | >50 | 32.35 |

Test Example 3

Evaluation of Inhibition Activity Against Pan-FGFR Mutants

The inhibition activity of N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1, as a representative compound of the present invention, against pan-FGFR mutants was measured. Enzymatic activity and cellular activity were measured. The result is shown in Table 3 and Table 4.

TABLE 3

| Mutant enzymes | FGFR1 mutant (V561M) | FGFR2 mutant (N549H) | FGFR3 mutant (K650E) |
|---|---|---|---|
| Compound of Example 1 | 10 nM | 901 nM | 4.8 nM |

TABLE 4

| Mutant cells | AN3-CA | MFE296 | SNU-16 | RT-112 | OPM-2 |
|---|---|---|---|---|---|
| Compound of Example 1 | 53 nM | 1600 nM | 2.7 nM | 29 nM | 43 nM |

Test Example 5

Evaluation of Microsomal Stability

The microsomal stability of N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1, as a representative compound of the present invention, was evaluated. The result is shown in Table 6.

TABLE 6

| Tested species | Time (min) | Compound of Example 1 | Positive control (midazolam) | Negative control (excluding NADPH) |
|---|---|---|---|---|
| Mouse | 0 | 100.00% | 100.00% | 100.00% |
| | 5 | 62.73% | 10.42% | 103.56% |
| | 10 | 40.77% | 1.13% | 103.56% |
| | 15 | 29.27% | 0.18% | 102.67% |
| | 30 | 11.88% | 0.05% | 106.67% |
| | 45 | 3.87% | — | 106.67% |
| | 60 | 3.64% | — | 104.44% |
| | T$_{1/2}$ (min) | 9.93 | NA | NA |
| Rat | 0 | 100.00% | 100.00% | — |
| | 5 | 95.53% | 13.65% | — |
| | 10 | 88.45% | 1.01% | — |
| | 15 | 82.61% | 0.14% | — |
| | 30 | 65.16% | 0.04% | — |
| | 45 | 45.27% | — | — |
| | 60 | 44.31% | — | — |
| | T$_{1/2}$ (min) | 39.56 | NA | NA |
| Dog | 0 | 100.00% | 100.00% | — |
| | 5 | 77.02% | 6.23% | — |
| | 10 | 57.41% | 0.59% | — |
| | 15 | 44.70% | 0.27% | — |
| | 30 | 21.03% | 0.10% | — |

TABLE 6-continued

| Tested species | Time (min) | Compound of Example 1 | Positive control (midazolam) | Negative control (excluding NADPH) |
|---|---|---|---|---|
| | 45 | 8.23% | — | — |
| | 60 | 5.02% | — | — |
| | $T_{1/2}$ (min) | 13.50 | NA | NA |
| Human | 0 | 100.00% | 100.00% | — |
| | 5 | 80.36% | 38.75% | — |
| | 10 | 76.63% | 12.92% | — |
| | 15 | 64.04% | 5.60% | — |
| | 30 | 51.45% | 0.73% | — |
| | 45 | 37.62% | — | — |
| | 60 | 36.17% | — | — |
| | $T_{1/2}$ (min) | 33.94 | NA | NA |

Test Example 6

In-Vivo PK Profile

The in-vivo PK profile (mouse PK/ICR mice and rat PK/Sprague-Dawley rat) of N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1 is as follows.

TABLE 7

| Mouse PK/ICR mice | | | | | | | | | |
|---|---|---|---|---|---|---|---|---|---|
| Dosage | $t_{1/2}$ hr | $T_{max}$ hr | $C_{max}$ ng/mL | $AUC_{(0-t)}$ ng/mL*hr | $AUC_{(0-\infty)}$ ng/mL*hr | Vz L/kg | CL L/hr/kg | $MRT_{(0-\infty)}$ hr | F* % |
| IV 5 mg/kg | 1.83 | 0.083 | 111.03 | 321.99 | 350.27 | 37.69 | 14.27 | 3.56 | — |
| PO 10 mg/kg | NA | 6.00 | 27.07 | 150.93 | NA | — | — | NA | 23.44 |

TABLE 8

| Rat PK/Sprague-Dawley rat | | | | | | | | | |
|---|---|---|---|---|---|---|---|---|---|
| Dosage | $t_{1/2}$ hr | $T_{max}$ hr | $C_{max}$ ng/mL | $AUC_{(0-t)}$ ng/mL*hr | $AUC_{(0-\infty)}$ ng/mL*hr | Vz L/kg | CL L/hr/kg | $MRT_{(0-\infty)}$ hr | F* % |
| IV 5 mg/kg | 5.75 | 0.083 | 270.95 | 844.42 | 884.29 | 47.99 | 5.84 | 6.37 | — |
| PO 5 mg/kg | 9.14 | 5.33 | 11.59 | 129.20 | 652.26 | — | — | 12.57 | 13.46 |

Test Example 7

Evaluation of In-Vivo Efficacy in Endometrial Cancer Cell Line-Transplanted Animal Model The in-vivo efficacy of N-(2,6-dichloro-3,5-dimethoxyphenyl)-1-(6-((4-(4-ethylpiperazin-1-yl)phenyl)amino)pyrimidin-4-yl)-1H-benz[d]imidazol-2-amine synthesized in Example 1 was evaluated as follows.

Four-to-five-week old BALB/C nude mouse transplanted with the FGFR2-overexpressed endometrial cancer cell line AN3-CA was used as an animal model. AZD4547 (AstraZeneca) known as an FGFR inhibitor was used as a control drug. A mixture solution (pH=4) of N-methylpyrrolidinone (NMP, 5%), Solutol (6%), polyethylene glycol (PEG 400, 20%) and distilled water (69%) was used as a vehicle. A result obtained by orally administering the drug once a day is shown in FIG. 1.

As described above, since the heteroarylamine compound represented by Chemical Formula 1 according to the present invention or a pharmaceutically acceptable salt thereof exhibits inhibition activity against protein kinases, it is useful for prevention and treatment of diseases caused by abnormal cell growth induced by protein kinases, for example, various tumor diseases selected from endometrial cancer, bladder cancer, stomach cancer, lung cancer, liver cancer, colon cancer, small intestine cancer, pancreatic cancer, brain cancer, bone cancer, melanoma, breast cancer, sclerosing adenosis, head and neck cancer, esophageal cancer, thyroid cancer, parathyroid cancer, kidney cancer, sarcoma, prostate cancer, urethral cancer, blood cancer such as leukemia, multiple myeloma and myelodysplastic syndrome, lymphoma such as Hodgkin's disease and non-Hodgkin lymphoma, fibroadenoma, etc.

What is claimed is:

1. A compound selected from a heteroarylamine compound represented by Chemical Formula 1, a pharmaceutically acceptable salt thereof, a hydrate thereof and a solvate thereof:

[Chemical Formula 1]

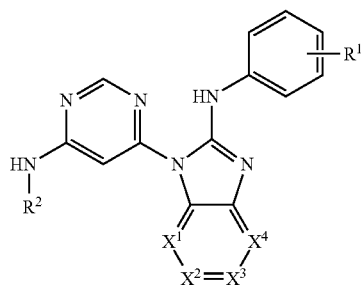

wherein,
$R^1$ is one to four substituent(s) selected from a halogen atom, $C_1$-$C_8$ alkyl, $C_1$-$C_8$ alkoxy and

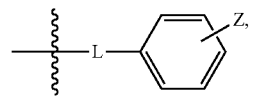

R² is a hydrogen atom, C₁-C₈ alkyl, —(CH₂)ₘ—NR³R⁴ or -A-(CH₂)ₙ-(Q)ₚ-R⁵,

A is C₆-C₁₅ aryl, 5- or 6-membered heteroaryl containing one to three nitrogen atom(s) or 5- or 6-membered heterocycloalkyl containing one to three heteroatom(s) selected from a nitrogen atom and an oxygen atom, wherein each of the aryl, heteroaryl or heterocycloalkyl may be substituted or unsubstituted with one to three substituent(s) selected from C₁-C₈ alkyl, C₁-C₈ alkoxy, C₁-C₈ haloalkyl and C₁-C₈ alkoxycarbonyl, L is —NHC(O)— or —C(O)NH—, Z is one to four substituent(s) selected from C₁-C₈ alkyl, C₁-C₈ haloalkyl, 5- or 6-membered heteroaryl containing one to three nitrogen atom(s) and 5- or 6-membered heterocycloalkyl containing one to three heteroatom(s) selected from a nitrogen atom and an oxygen atom, wherein the heteroaryl or heterocycloalkyl may be substituted or unsubstituted with C₁-C₈ alkyl, Q is 5- or 6-membered heterocycloalkyl or biheterocycloalkyl containing one to three heteroatom(s) selected from a nitrogen atom and an oxygen atom, each of R³ and R⁴ is a hydrogen atom or C₁-C₈ alkyl, R⁵ is a hydrogen atom, C(O)OR⁷ (wherein R⁷ is a hydrogen atom or C₁-C₈ alkyl) or C₁-C₈ alkyl, m is an integer from 1 to 6, n is an integer from 0 to 6, p, which indicates the presence or absence of Q, is 0 or 1, and wherein X¹ and X⁴ are N and X² and X³ are CH.

2. The compound according to claim 1, wherein R¹ is one to four substituent(s) selected from chloro, methyl, methoxy, —NHC(O)-(3-trifluoromethylbenzene) and —C(O)NH-(3-trifluoromethylbenzene).

3. The compound according to claim 1, wherein R² is a hydrogen atom.

4. The compound according to claim 1, wherein R² is methyl, ethyl or cyclopropyl.

5. The compound according to claim 1, wherein R² is 2-(dimethylamino)ethyl or 3-(dimethylamino)propyl.

6. The compound according to claim 1, wherein R² is phenyl, methoxy-substituted phenyl, trifluoromethyl-substituted phenyl, methoxy- and methoxycarbonyl-substituted phenyl, pyridinyl, pyrimidinyl, 4-methylpiperidin-1-yl or 4-ethylpiperidin-1-yl.

7. The compound according to claim 1, wherein R² is

[Structure]

and wherein each of X and Y, which are identical to or different from each other, is CH or N, Q is piperidinyl, bipiperidinyl, piperazinyl or morpholino, R⁵ is a hydrogen atom, methyl, ethyl, cyclohexylmethyl or methoxycarbonyl, R⁶ is a hydrogen atom, methoxy, trifluoromethyl or methoxycarbonyl and n is an integer from 0 to 3.

8. A compound selected from a heteroarylamine compound represented by Chemical Formula 1, a pharmaceutically acceptable salt thereof, a hydrate thereof and a solvate thereof;

[Chemical Formula 1]

[Structure]

wherein,

R¹ is one to four substituent(s) selected from a halogen atom, C₁-C₈ alkyl, C₁-C₈ alkoxy and

[Structure]

R² is a hydrogen atom, C₁-C₈ alkyl, —(CH₂)ₘ—NR³R⁴ or -A-(CH₂)ₙ-(Q)ₚ-R⁵,

A is C₆-C₁₅ aryl, 5- or 6-membered heteroaryl containing one to three nitrogen atom(s) or 5- or 6-membered heterocycloalkyl containing one to three heteroatom(s) selected from a nitrogen atom and an oxygen atom, wherein each of the aryl, heteroaryl or heterocycloalkyl may be substituted or unsubstituted with one to three substituent(s) selected from C₁-C₈ alkyl, C₁-C₈ alkoxy, C₁-C₈ haloalkyl and C₁-C₈ alkoxycarbonyl, L is —NHC(O)— or —C(O)NH—, Z is one to four substituent(s) selected from C₁-C₈ alkyl, C₁-C₈ haloalkyl, 5- or 6-membered heteroaryl containing one to three nitrogen atom(s) and 5- or 6-membered heterocycloalkyl containing one to three heteroatom(s) selected from a nitrogen atom and an oxygen atom, wherein the heteroaryl or heterocycloalkyl may be substituted or unsubstituted with C₁-C₈ alkyl, Q is 5- or 6-membered heterocycloalkyl or biheterocycloalkyl containing one to three heteroatom(s) selected from a nitrogen atom and an oxygen atom, each of R³ and R⁴ is a hydrogen atom or C₁-C₈ alkyl, R⁵ is a hydrogen atom, C(O)OR⁷ (wherein R⁷ is a hydrogen atom or C₁-C₈ alkyl) or C₁-C₈ alkyl, m is an integer from 1 to 6, n is an integer from 0 to 6, and p, which indicates the presence or absence of Q, is 0 or 1, wherein X¹ and X⁴ are N and X² and X³ are CH, and wherein the compound of Chemical Formula 1 is N-(3,5-dimethoxyphenyl)-1-(6-((4-(4-ethylpiperazin-1-yl)phenyl)amino)pyrimidin-4-yl)-1H-imidazo[4,5-b]pyrazin-2-amine or N-(3-((1-(6-((4-(4-ethylpiperazin-1-yl)phenyl)amino)pyrimidin-4-yl)-1H-imidazo[4,5-b]pyrazin-2-yl)amino)-4-methylphenyl)-3-(trifluoromethyl)benzamide.

9. A method of treating a tumor disease selected from the group consisting of endometrial cancer, bladder cancer, stomach cancer, lung cancer, liver cancer, colon cancer, small intestine cancer, pancreatic cancer, brain cancer, bone cancer, melanoma, breast cancer, sclerosing adenosis, head and neck cancer, esophageal cancer, thyroid cancer, parathyroid cancer, kidney cancer, sarcoma, prostate cancer, urethral cancer, leukemia, multiple myeloma, blood cancer, lymphoma and fibroadenoma, in a patient comprising administering to the patient a compound according to claim 1.

10. A method of inhibiting the proliferation of a cell line selected from the group consisting of AN3-CA, MFE296, SNU-16, RT112 or OPM-2 comprising contacting the cell line with a compound according to claim 1.

11. A compound selected from a heteroarylamine compound represented by Chemical Formula 1, a pharmaceutically acceptable salt thereof, a hydrate thereof and a solvate thereof:

[Chemical Formula 1]

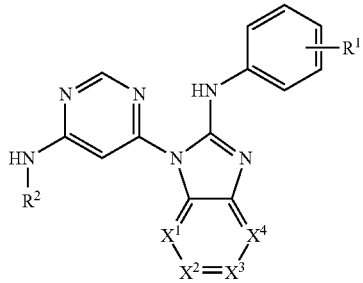

wherein $R^1$ is one to four substituent(s) selected from a halogen atom, $C_1$-$C_8$ alkyl, $C_1$-$C_8$ alkoxy and

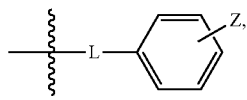

$R^2$ is a hydrogen atom, $C_1$-$C_8$ alkyl, —$(CH_2)_m$—$NR^3R^4$ or -A-$(CH_2)_n$-$(Q)_p$-$R^5$, A is $C_6$-$C_{15}$ aryl, 5- or 6-membered heteroaryl containing one to three nitrogen atom(s) or 5- or 6-membered heterocycloalkyl containing one to three heteroatom(s) selected from a nitrogen atom and an oxygen atom, wherein each of the aryl, heteroaryl or heterocycloalkyl may be substituted or unsubstituted with one to three substituent(s) selected from $C_1$-$C_8$ alkyl, $C_1$-$C_8$ alkoxy, $C_1$-$C_8$ haloalkyl and $C_1$-$C_8$ alkoxycarbonyl, L is —NHC(O)— or —C(O)NH—, Z is one to four substituent(s) selected from $C_1$-$C_8$ alkyl, $C_1$-$C_8$ haloalkyl, 5- or 6-membered heteroaryl containing one to three nitrogen atom(s) and 5- or 6-membered heterocycloalkyl containing one to three heteroatom(s) selected from a nitrogen atom and an oxygen atom, wherein the heteroaryl or heterocycloalkyl may be substituted or unsubstituted with $C_1$-$C_8$ alkyl, Q is 5- or 6-membered heterocycloalkyl or biheterocycloalkyl containing one to three heteroatom(s) selected from a nitrogen atom and an oxygen atom, each of $R^3$ and $R^4$ is a hydrogen atom or $C_1$-$C_8$ alkyl, $R^5$ is a hydrogen atom, C(O)$OR^7$ (wherein $R^7$ is a hydrogen atom or $C_1$-$C_8$ alkyl) or $C_1$-$C_8$ alkyl, m is an integer from 1 to 6, n is an integer from 0 to 6, p, which indicates the presence or absence of Q, is 0 or 1, and wherein $X^1$, $X^3$ and $X^4$ are CH and $X^2$ is N.

* * * * *